(12) United States Patent
Majeed et al.

(10) Patent No.: US 10,260,112 B2
(45) Date of Patent: Apr. 16, 2019

(54) PCR PRIMERS AND METHODS THEREOF FOR THE IDENTIFICATION OF BACILLUS COAGULANS

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN)

(73) Assignee: SAMI LABS LIMITED, Bangalore (IN)

(*) Notice: Subject to any disclaimer, the term of this patent is extended or adjusted under 35 U.S.C. 154(b) by 197 days.

(21) Appl. No.: 15/276,912

(22) Filed: Sep. 27, 2016

(65) Prior Publication Data
US 2017/0096700 A1    Apr. 6, 2017

Related U.S. Application Data

(60) Provisional application No. 62/235,593, filed on Oct. 1, 2015.

(51) Int. Cl.
*C12P 19/34* (2006.01)
*C12Q 1/689* (2018.01)

(52) U.S. Cl.
CPC ....... *C12Q 1/689* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2008/0026368 A1* 1/2008 Snaidr .................. C12Q 1/689
435/134

OTHER PUBLICATIONS

Kovacs et al., Functional Analysis of the ComK Protein of Bacillus coagulans, Jan. 2013, vol. 8, issue 1, pp. 1-12. (Year: 2013).*

* cited by examiner

*Primary Examiner* — Kenneth R Horlick

(57) ABSTRACT

The present invention discloses novel oligonucleotide primer sequences BC1, BC2 and BC3 for the identification of *Bacillus coagulans*. The invention also discloses a PCR based method for the identification of *Bacillus coagulants* using the aforesaid primers, wherein positive amplification with primer sets BC1, BC2 and negative amplification with primer set BC3 confirms the presence of *Bacillus coagulans*.

6 Claims, 2 Drawing Sheets
Specification includes a Sequence Listing.

PCR PRIMERS AND METHODS THEREOF FOR THE IDENTIFICATION OF BACILLUS COAGULANS

CROSS-REFERENCE TO RELATED APPLICATIONS

This application is a non-provisional filing for U.S. provisional application No. 62/235,593 filed on 1 Oct. 2015.

FIELD OF THE INVENTION

The invention in general relates to field of molecular biology and probiotic lactic acid bacteria—*Bacillus coagulans*. More specifically, the invention relates to (i) Novel oligonucleotide primers for the identification of *Bacillus coagulans* (ii) A Polymerase Chain Reaction (PCR) based method using the aforesaid primers for the identification of *Bacillus coagulans*.

BACKGROUND OF THE INVENTION

Description of Prior Art

Probiotics are now being used extensively as food supplements for the effective management of intestinal and urinary tract infections. Probiotic bacteria of the genera *Bifidobacterium* and *Lactobacilli* are being marketed in the form of oral supplements by many commercial players. Since the probiotic activity is linked to the type of bacterial species/strain, it is imperative to identify the type of bacterial species/strain in the probiotic supplement. It is also imperative to identify and differentiate probiotic bacterium from other pathogenic *Bacillus* species which could contaminate milk, milk products and other supplements.

*Bacillus coagulans* is one of the widely used probiotic supplement. The US food and Drug Administration (FDA) has listed *Bacillus coagulans* as one of the bacteria that contaminates canned food (Landry et al. (2001) Bacteriological Analytical Manual Chapter 21A Examination of Canned Foods In: BAM: Examination of Canned Foods). The biological importance of *B. coagulans* as probiotics and contaminants calls for effective identification of the organism. Methods to identify *B. coagulans* using molecular techniques like polymerase chain reaction (Lei et al., Method for identifying *Bacillus coagulans*, CN104004846), Real time PCR (Liu et al., Fluorescence quantitative polymerase chain reaction (PCR) method for detecting *Bacillus coagulans* quickly, CN102304559), PCR-RAPD (Sudha et al., (2010) Molecular Typing and Probiotic Attributes of a New Strain of *Bacillus coagulans*—Unique IS-2: A Potential Biotherapeutic Agent, Genetic Engineering and Biotechnology Journal, 2010:1-20), PCR—Denaturing gradient gel electrophoresis (Theunissen et al., (2005), Identification of probiotic microorganisms in South African products using PCR based DGGE analysis, International Journal of Food Microbiology, 98(1):11-21) are well known in the state of art. Most of the studies identify *Bacillus coagulans* by targeting the difference in the 16s rRNA sequence between the *Bacillus* species. Oligonucleotide primers for Identifying *Bacillus coagulans* by targeting difference in other functional genes between species are in need for fast and reliable mode of detection. The present invention solves this technical problem by disclosing a sensitive PCR based method for the identification of *Bacillus coagulans* using novel primers by targeting the difference in the functional genes of *Bacillus* species.

It is the principle objective of the invention to disclose the use of novel oligonucleotide primers for the identification of *Bacillus coagulans*.

It is yet another objective of the present invention to disclose a PCR based method for the identification of *Bacillus coagulans* using the aforesaid primers.

The present invention fulfils the aforesaid objectives and provides further related advantages.

SUMMARY OF THE INVENTION

Disclosed is (i) novel oligonucleotide primers BC1 (comprising forward primer sequence ID1 and reverse primer of sequence ID2), BC2 (comprising forward primer of 2 sequence ID3 and reverse primer of sequence ID4), BC3 (comprising forward primer of sequence ID5 and reverse primer of sequence ID6), for the identification of *Bacillus coagulans*; and (ii) A PCR based method for the identification *Bacillus coagulans* using aforesaid primers wherein positive amplification with primer sets BC1, BC2 and negative amplification with primer set BC3 confirms the presence of *Bacillus coagulans*.

Other features and advantages of the present invention will become apparent from the following more detailed description, taken in conjunction with the accompanying images, which illustrate, by way of example, the principle of the invention.

DESCRIPTION OF THE MOST PREFERRED EMBODIMENTS

Figure 1:
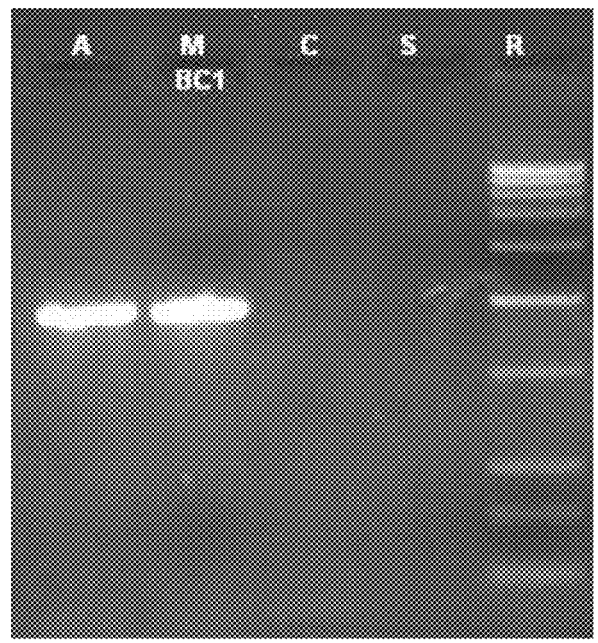
FIG. 1 shows the agarose gel (2%) electrophoresis image showing the PCR product after amplification using Primer set BC1. Lane A denotes *Bacillus coagulans* ATCC 31284; Lane M denotes *Bacillus coagulans* ATCC 5856; Lane C denotes *Bacillus cereus* ATCC 14579; Lane S denotes *Bacillus subtilis* MTCC 441; and Lane R denotes DNA Ladder with fragments of 0.1, 0.2, 0.3, 0.6, 1, 1.5, 2, 2.5 and 3 Kb.

In the most preferred embodiment, the present invention discloses novel primer sequences comprising:
a) Primer BC 1 comprising of forward primer as in sequence ID 1 and reverse primer as in sequence ID 2;
b) Primer BC 2 comprising of forward primer as in sequence ID 3 and reverse primer as in sequence ID 4;
c) Primer BC 3 comprising of forward primer as in sequence ID 5 and reverse primer as in sequence ID 6.
for the identification of *Bacillus coagulans*.

In another preferred embodiment, the invention discloses a method of identifying *Bacillus coagulans* using a Polymerase Chain Reaction (PCR), said method comprising steps of isolating DNA from *Bacillus coagulans* and amplifying isolated DNA using aforementioned primers by incubation at 94° C. for 30 seconds (1 cycle), followed by 30 cycles at 94° C. for 30 seconds, annealing temperature for 30 seconds, and at 72° C. for 1 minute, followed by a final incubation at 72° C. for 5 minutes (1 cycle) with a hold at 4° C.

In a related embodiment, the annealing temperature of primer BC1 comprising forward primer as in Sequence ID 1 and reverse primer as in Sequence ID 2 is 60° C. and gives an amplification product of ~990 base pairs. In another related embodiment, the annealing temperature of primer BC2 comprising forward primer as in Sequence ID 3 and reverse primer as in Sequence ID 4 is 58° C. and gives an amplification product of ~543 base pairs. In yet another embodiment of the invention, the annealing temperature of primer sequence BC3 comprising forward primer as in Sequence ID 5 and reverse primer as in Sequence ID 6 is 68° C. and gives an amplification product of ~3010 base pairs.

In another embodiment, the invention discloses a process for identifying *Bacillus coagulans*, wherein a positive amplification for primer BC1, primer BC2 and negative amplification for primer BC3 confirms the presence of *Bacillus coagulans*.

The process disclosed herein identifies all strains of *Bacillus coagulans* including *Bacillus coagulans* MTCC 5856, *Bacillus coagulans* ATCC 31284, *Bacillus coagulans* ATCC 7050, *Bacillus coagulans* 2-6, *Bacillus coagulans* 36D1, *Bacillus coagulans* S-lac and *Bacillus coagulans* HM-08 among others and also differentiates from all other species of *Bacillus* genera including *Bacillus cereus* and *Bacillus subtilis* among others.

The specific examples included herein below illustrate the aforesaid most preferred embodiments of the present invention.

Example I: Primer Design and Synthesis

The unique regions of *Bacillus coagulans* strains were determined by extensive data mining of whole genome of all available whole genome sequences in the data base and compared with *Bacillus coagulans* MTCC 5856. Three specific regions were selected based on the initial analysis of data and compared with *Bacillus subtilis* and *Bacillus cereus* In-silico analysis of data suggested that these regions were common in all *Bacillus coagulans* strains but did not present in other *Bacillus* species.

The possible gene targets for the synthesis of primers to identify *Bacillus coagulans*, based on the in-silico results are represented in Table 1. The target genes for the design of primers were selected based on their similarity among *Bacillus coagulans* and dissimilarity among other *Bacillus* species i.e. *Bacillus subtilis* and *Bacillus cereus*.

TABLE 1

| S. No | Primers | Target genes | Possible functional protein | Target Organism |
|---|---|---|---|---|
| 1 | BC1 | marC | marC integral membrane family protein. Hypothetical protein AB434_0121. Hypothetical protein SB48_HM08orf01623. Hypothetical protein AB434_0122. Hypothetical protein SB48_HM08orf05756. hypothetical protein Bcoa_0848 | *Bacillus coagulans* |

TABLE 1-continued

| S. No | Primers | Target genes | Possible functional protein | Target Organism |
|---|---|---|---|---|
| 2 | BC2 | comK | disA bacterial checkpoint controller nucleotide-binding family protein. comK family protein | *Bacillus coagulans* |
| 3 | BC3 | Tsr, Trg and Tap | Methyl-accepting chemotaxis sensory transducer with Cache sensor. Chemotaxis protein. Methyl-accepting chemotaxis protein. glycogen/starch/alpha-glucan phosphorylases family protein | *Bacillus coagulans* |

The sequence of Primer BC1 was synthesised using the marC integral membrane family protein gene as template. The gene encodes a protein marC that spans the plasma membrane multiple times and once was thought to be a multiple antibiotic resistance protein. A later study identified that the protein was not involved in multiple antibiotic resistance. The exact function of this gene family is still unclear (McDermott et al., (2008), The marC gene of *Escherichia coli* is not involved in multiple antibiotic resistance, Antimicrobial Agents and Chemotherapy, 52:382-383). The forward and reverse primers as in Sequence ID 1 and Sequence ID 2 were designed by using Primer3web version 4.0.0 (Untergasser et al., (2012) Primer3—new capabilities and interfaces. *Nucleic Acids Research* 40(15): e115) which gives an amplification product (Sequence ID 7) of ~990 base pairs. The selected primer sequences were synthesised and obtained from Eurofins Scientific, Bangalore, India.

Basic Local Alignment Search Tool (BLAST) search of the amplified sequence (Sequence ID 7) indicated that the Primer BC1 comprising of forward primer as in Sequence ID 1 and reverse primer as in Sequence ID 2 could specifically identify all strains of *Bacillus coagulans* (Table 2) and can differentiate *Bacillus coagulans* from other *Bacillus* species.

TABLE 2

BLAST result of sequences producing significant alignments with DNA sequence amplified by Primer BC1

| Description | Max Score | Total Score | Query cover | E value | Identity | Accession |
|---|---|---|---|---|---|---|
| *Bacillus coagulans* strain S- lac, complete genome | 1829 | 2211 | 100% | 0.0 | 100% | CP011939.1 |
| *Bacillus coagulans* strain HM08, complete genome | 1829 | 2211 | 100% | 0.0 | 100% | CP010525.1 |
| *Bacillus coagulans* 36D1, complete genome | 1829 | 2211 | 100% | 0.0 | 100% | CP003056.1 |
| *Bacillus coagulans* 26, Complete genome | 1112 | 1112 | 75% | 0.0 | 93% | CP002472.1 |
| *Bacillus coagulans* DSM 1 = ATCC 7050, complete genome | 1107 | 1107 | 75% | 0.0 | 93% | CP009709.1 |

The sequence of Primer BC2 was synthesised using the ComK family protein gene as template. ComK of *Bacillus* species is a positive auto-regulatory protein occupying a central position in the competence-signal-transduction network. It positively regulates the transcription of late competence genes, which specify morphogenetic and structural proteins necessary for construction of the DNA-binding and uptake apparatus, as well as the transcription of comK itself (Kovacs et al., (2013), Functional Analysis of the ComK Protein of *Bacillus coagulans*. PLoS ONE 8(1): e53471). The forward and reverse primers as in Sequence ID 3 and Sequence ID 4 were designed by using Primer3web version 4.0. (Untergasser et al., (2012) Primer3—new capabilities and interfaces. *Nucleic Acids Research* 40(15):e115) which gives an amplification product (Sequence ID 8) of ~543 base pairs. The selected primer sequences were synthesised and obtained from Eurofins Scientific, Bangalore, India.

Basic Local Alignment Search Tool (BLAST) search of the amplified sequence (Sequence ID 8) indicated that the Primer BC2 comprising of forward primer as in Sequence ID 3 and reverse primer as in Sequence ID 4 could specifically identify all strains of *Bacillus coagulans* (Table 3) and can differentiate *Bacillus coagulans* from other *Bacillus* species.

TABLE 3

BLAST result of sequences producing significant alignments with DNA sequence amplified by Primer BC2

| Description | Max Score | Total Score | Query cover | E value | Identity | Accession |
|---|---|---|---|---|---|---|
| *Bacillus coagulans* DSM 1 = ATCC 7050, complete genome | 1003 | 1003 | 100% | 0.0 | 100% | CP009709.1 |
| *Bacillus coagulans* DSM 1 = ATCC 7050, ComK (comK) gene, complete cds | 1003 | 1003 | 100% | 0.0 | 100% | JX518619.1 |
| *Bacillus coagulans* 26, Complete genome | 981 | 981 | 100% | 0.0 | 99% | CP002472.1 |

TABLE 3-continued

BLAST result of sequences producing significant alignments with DNA sequence amplified by Primer BC2

| Description | Max Score | Total Score | Query cover | E value | Identity | Accession |
|---|---|---|---|---|---|---|
| *Bacillus coagulans* 36D1, complete genome | 837 | 837 | 100% | 0.0 | 94% | CP003056.1 |
| *Bacillus coagulans* strain S- lac, complete genome | 809 | 809 | 100% | 0.0 | 94% | CP011939.1 |
| *Bacillus coagulans* strain HM08, complete genome | 809 | 809 | 100% | 0.0 | 94% | CP010525.1 |

The sequence of Primer BC3 was synthesised using the Methyl-accepting chemotaxis protein (MCP) gene as template. Methyl-accepting chemotaxis protein (MCP) is a transmembrane sensor protein of bacteria. Use of the MCP allows bacteria to detect concentrations of molecules in the extracellular matrix so that the bacteria may smooth swim or tumble accordingly. If the bacteria detects rising levels of attractants (nutrients) or declining levels of repellents (toxins), the bacteria will continue swimming forward or smooth swimming. If the bacteria detect declining levels of attractants or rising levels of repellents, the bacteria will tumble and re-orient itself in a new direction. In this manner, a bacterium may swim towards nutrients and away from toxins (Derr et al., (2006) Changing the specificity of a bacterial chemoreceptor, Journal of Molecular Biology, 355 (5): 923-32). The forward and reverse primers as in Sequence ID 5 and Sequence ID 6 were designed by using Primer3web version 4.0.0 (Untergasser et al., (2012) Primer3—new capabilities and interfaces. *Nucleic Acids Research* 40(15):e115) which gives an amplification product (Sequence ID 9) of ~3010 base pairs. The selected primer sequences were synthesised and obtained from Eurofins Scientific, Bangalore, India.

Basic Local Alignment Search Tool (BLAST) search of the amplified sequence (Sequence ID 9) indicated that the Primer BC3 comprising of forward primer as in Sequence ID 5 and reverse primer as in Sequence ID 6 could specifically identify all strains of *Bacillus coagulans* Table 4).

TABLE 4

BLAST result of sequences producing significant alignments with DNA sequence amplified by Primer BC2

| Description | Max Score | Total Score | Query cover | E value | Identity | Accession |
|---|---|---|---|---|---|---|
| *Bacillus coagulans* strain S- lac, complete genome | 5559 | 5559 | 100% | 0.0 | 100% | CP011939.1 |
| *Bacillus coagulans* strain HM08, complete genome | 5559 | 5559 | 100% | 0.0 | 100% | CP010525.1 |
| *Bacillus coagulans* 36D1, complete genome | 5424 | 5424 | 99% | 0.0 | 99% | CP003056.1 |
| *Bacillus coagulans* 26, Complete genome | 3954 | 3954 | 93% | 0.0 | 92% | CP002472.1 |

TABLE 4-continued

BLAST result of sequences producing significant alignments
with DNA sequence amplified by Primer BC2

| Description | Max Score | Total Score | Query cover | E value | Identity | Accession |
|---|---|---|---|---|---|---|
| *Bacillus coagulans* DSM 1 = ATCC 7050, complete genome | 3916 | 4005 | 96% | 0.0 | 92% | CP009709.1 |
| *Syntrophobacter fumaroxidans* MPOB, complete genome | 73.1 | 73.1 | 4% | 4E−08 | 77% | CP000478.1 |

Example II: Sample Preparation

DNA Isolation

Weighed 1.0 gm of *Bacillus coagulans* MTCC 5856 (LactoSpore® 15 billion spores/gm), *Bacillus coagulans* ATCC 31284; *Bacillus cereus* ATCC 14579; *Bacillus subtilis* and added to 250 ml of sterile saline (0.9 gm NaCl, w/v) separately and diluted serially using sterile saline. The recommended dilution is $250 \times 10^6$ to obtain 30-300 colonies per plate. Incubated the diluted samples in water bath for 30 min at 75° C., and cooled immediately to below 45° C. Then, dispensed 1.0 mL of above sample to each of five sterile Petri plates and then poured 15 to 20 ml of previously cooled Glucose Yeast Extract Media (around 45° C.) to each plate. Rotated and swirled the plates to form a uniform spread and allow it to solidify. The plates were then incubated at 37° C.±2° C. for 48 to 72 hours. The pure isolated colonies grown on plates were then removed carefully using a sterile loop. Further, the cells removed from the plates were suspended in 100 μL, of PBS reagent in a 2.0-mL microcentrifuge tube. Added 2 μl of lysozyme solution (10 mg/ml) mixed by finger flicking and incubated the tubes at 37° C. for 10 minutes till the cells became clumpy. Then 300 μl DNAzol (Guanidium thiocyanate, Sarkosyl and Tris buffer-commercially available from Thermo Fisher Scientific (catalogue number 10503-027) was added and the tubes were vortexed for 10 s-30 s or until the cells are homogeneously suspended in the Reagent. The mixture was then heated for 10 min in a water bath held at 100° C. and centrifuged for 5 min at 16,000×g. The supernatant was carefully transferred to a new microcentrifuge tube. This solution contains the bacterial genomic DNA. Before analysis, the samples were prepared by diluting an aliquot of this solution with sterile TE (10 mM TrisHCl (pH7.4) and 1 mM EDTA-1:50, v/v). This will yield DNA of about 10-100 ng/μl.

Preparation of Primers

Primer BC1: The primer BC1 comprising of forward primer as in Sequence ID1 and reverse primer as in Sequence ID2 were diluted to 100 μmol/mL in sterile 10 mM TrisHCl pH 7.4 and 0.1 mM EDTA buffer, and stored at −20° or −80°. Immediately before use, diluted an aliquot of each primer with sterile water or TE buffer with 0.1 mM EDTA (1:10, v/v). The annealing temperature for Primer set BC1 is 60°. A positive test for Primer set BC1 is expected to give an amplification product of ~990 base pairs (Sequence ID 7).

Primer BC2: The primer BC2 comprising of forward primer as in Sequence ID3 and reverse primer as in Sequence ID4 were diluted to 100 μmol/mL in sterile 10 mM TrisHC1 pH 7.4 and 0.1 mM EDTA buffer and stored at −20° or −80°. Immediately before use, dilutes an aliquot of each primer with sterile water or TE buffer with 0.1 mM EDTA (1:5, v/v). The annealing temperature for Primer set BC2 is 58° C. A positive test for Primer set BC2 is expected to give an amplification product of ~543 base pairs (Sequence ID8).

Primer BC3: The primer BC3 comprising of forward primer as in Sequence ID5 and reverse primer as in Sequence ID6 were diluted to 100 μmol/mL in sterile 10 mM TrisHCl pH 7.4 and 0.1 mM EDTA buffer and stored at −20° or −80°. Immediately before use, dilute an aliquot of each primer with sterile water or TE buffer with 0.1 mM EDTA (1:10, v/v). The annealing temperature for Primer set BC3 is 68° C. A positive test for Primer set, BC3 is expected to give an amplification product of 3 Kb (Sequence ID9).

Example III: PCR Amplification

For each Primer set, PCR sample was prepared by mixing 25 μL of 2×PCR master mix (1×PCR master mix has 0.1 mM each of dNTPs, 1× Taqpol assay buffer and 1 U of Taq Polymerase), 1 μL of diluted forward and reverse primer (10-20 picomoles), 1 μL of diluted Sample containing template DNA (approximately 10 ng-100 ng), and 22 μL of sterile water. PCR negative control was prepared by replacing the 1 μL of diluted Sample with 1 μL of nuclease-free water.

PCR amplification was carried out using an appropriate thermal cycler by the following steps:
1. Incubation at 94° C. for 30 s (1 cycle),
2. Denaturation at 94° C. for 30 s, Annealing temperature for 30 s, and extension at 72° C. for 1 min (30 Cycles)
3. Final incubation at 72° for 5 min (1 cycle) with a hold at 4° C.

The products of the PCR amplification for each PCR sample preparation and for the PCR negative control were analysed by performing an Agarose gel electrophoresis (2% agarose gel) and the DNA bands were visualised in a gel documentation system.

Acceptance Criteria

Primer BC1: The PCR sample preparation prepared with Primer set BC1 gives an amplification product of ~990 base pairs (positive). [FIG. 1]

Figure 2:
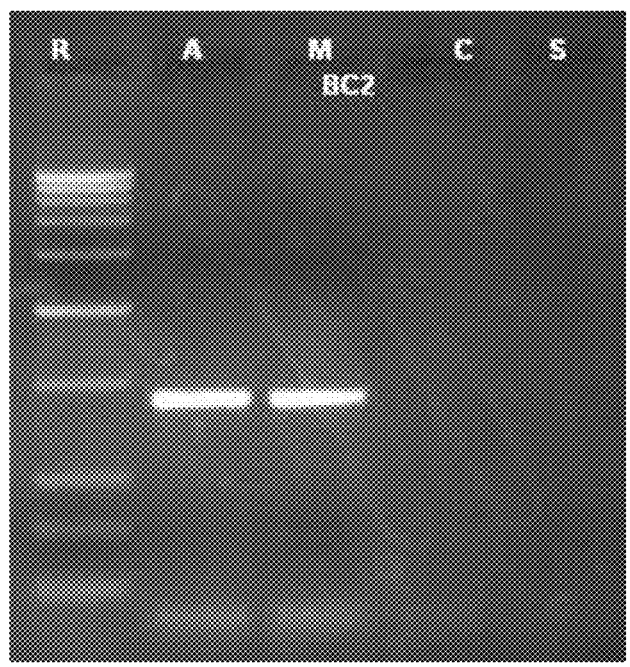
FIG. 2 shows the agarose gel (2%) electrophoresis image showing the PCR product after amplification using Primer set BC2. Lane A denotes *Bacillus coagulans* ATCC 31284; Lane M denotes *Bacillus coagulans* ATCC 5856; Lane C denotes *Bacillus cereus* ATCC 14579; Lane S denotes *Bacillus subtilis* MTCC 441; and Lane R denotes DNA Ladder with fragments of 0.1, 0.2, 0.3, 0.6, 1, 1.5, 2, 2.5 and 3 Kb.

Primer BC2: The PCR sample preparation prepared with Primer set BC2 gives the expected amplification product of ~543 base pairs (positive). [FIG. 2]

Figure 3:
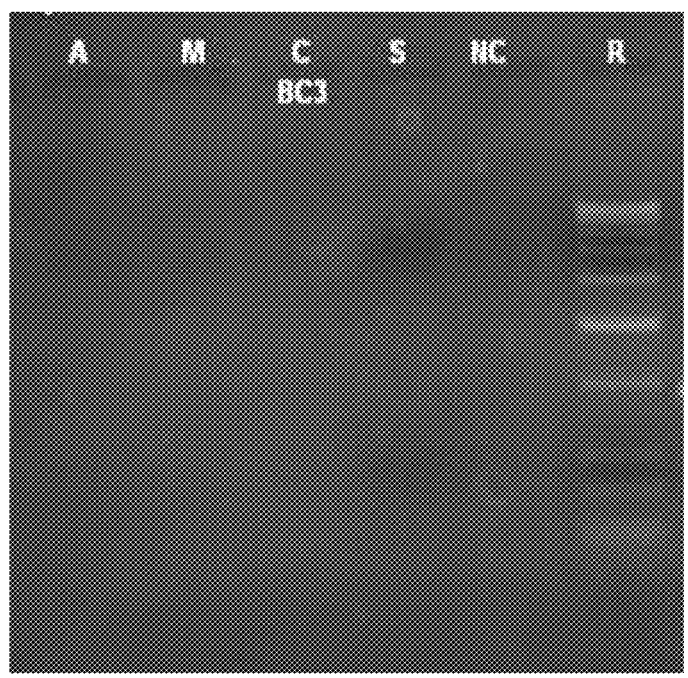
FIG. 3 shows the agarose gel (2%) electrophoresis image showing the PCR product after amplification using Primer set BC3. Lane A denotes *Bacillus coagulans* ATCC 31284; Lane M denotes *Bacillus coagulans* ATCC 5856; Lane C denotes *Bacillus cereus* ATCC 14579; Lane S denotes *Bacillus subtilis* MTCC 441; and Lane R denotes DNA Ladder with fragments of 0.1, 0.2, 0.3, 0.6, 1, 1.5, 2, 2.5 and 3 Kb.

Primer BC3: The PCR sample preparation prepared with Primer set BC3 DOES. NOT give an amplification product of ~3010 base pairs (negative). [FIG. 3]

The present invention discloses a process for identifying *Bacillus coagulans*, wherein a positive amplification for primer BC1, primer BC2 and negative amplification for primer BC3 confirms the presence of *Bacillus coagulans* and differentiates from other *Bacillus* species like *Bacillus* cereus and *Bacillus subtilis*. The invention would help in identifying *Bacillus coagulans* in the food, which includes, but not restricted to, food supplements, milk and milk products, beverages, confectionary, canned foods and in brewery.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method for identifying *Bacillus coagulans* using Polymerase Chain Reaction, comprising step of isolating DNA from *Bacillus coagulans* strains and amplifying the isolated DNA in a thermo cycler using novel primer sets BC1, BC2 and BC3, by incubating at 94° C. for 30 seconds (1 cycle), followed by 30 cycles at 94° C. for 30 seconds, at primer specific annealing temperature for 30 seconds, and at 72° C. for 1 minute, followed by a final incubation at 72° C. for 5 minutes with a hold at 4° C.

2. The method as in claim 1, wherein the annealing temperature of primer set BC1 comprising forward primer as in Sequence ID 1 and reverse primer as in Sequence ID 2 is 60° C. with an expected amplification product of ~990 base pairs, wherein Sequence ID 1 is 5' ACAGGGCTTTCAGA-TACCCG 3' and Sequence ID 2 is 5' CGGGGATCCGTC-CATCAAAA 3'.

3. The method as in claim 1, wherein the annealing temperature of primer set BC2 comprising forward primer as in Sequence ID 3 and reverse primer as in Sequence ID 4 is 58° C. with an expected amplification product of ~543 base pairs, wherein Sequence ID 3 is 5' GAATGCATTATG-CAACATGGG 3' and Sequence ID 4 is 5' CCAGGCT-TAAATCCAATACAG 3'.

4. The method as in claim 1, wherein the annealing temperature of primer set BC3 comprising forward primer as in Sequence ID 5 and reverse primer as in Sequence ID 6 is 68° C. with an expected amplification product of ~3010 base pairs, wherein Sequence ID 5 is 5' CGCCAAGCGGG-TACGCTTCACCG 3' and Sequence ID 6 is 5' AGAAATATAAGTTTTAAAGAAG 3'.

5. The method as in claim 1, wherein a positive amplification for primer set BC1, primer set BC2 and negative amplification for primer set BC3 confirms the presence of *Bacillus coagulans*.

6. The method as in claim 1, wherein the *Bacillus coagulans* strain is selected from the group consisting of *Bacillus coagulans* MTCC 5856, *Bacillus coagulans* ATCC 31284, *Bacillus coagulans* ATCC 7050, *Bacillus coagulans* 2-6, *Bacillus coagulans* 36D1, *Bacillus coagulans* S-lac and *Bacillus coagulans* HM-08.

* * * * *

```
                              SEQUENCE LISTING

<160> NUMBER OF SEQ ID NOS: 9

<210> SEQ ID NO 1
  <211> LENGTH: 20
  <212> TYPE: DNA
  <213> ORGANISM: Artificial Sequence
  <220> FEATURE:
  <223> OTHER INFORMATION: Synthesised forward primer of BC1

<400> SEQUENCE: 1
acagggcttt cagatacccg                                              20

<210> SEQ ID NO 2
  <211> LENGTH: 20
  <212> TYPE: DNA
  <213> ORGANISM: Artificial Sequence
  <220> FEATURE:
  <223> OTHER INFORMATION: Synthesised reverse primer of BC1

<400> SEQUENCE: 2
cggggatccg tccatcaaaa                                              20

<210> SEQ ID NO 3
  <211> LENGTH: 21
  <212> TYPE: DNA
  <213> ORGANISM: Artificial Sequence
  <220> FEATURE:
  <223> OTHER INFORMATION: Synthesised forward primer of BC2

<400> SEQUENCE: 3
gaatgcatta tgcaacatgg g                                            21

<210> SEQ ID NO 4
  <211> LENGTH: 21
  <212> TYPE: DNA
  <213> ORGANISM: Artificial Sequence
  <220> FEATURE:
  <223> OTHER INFORMATION: Synthesised reverse primer of BC2

<400> SEQUENCE: 4
ccaggcttaa atccaataca g                                            21

<210> SEQ ID NO 5
  <211> LENGTH: 23
  <212> TYPE: DNA
  <213> ORGANISM: Artificial Sequence
  <220> FEATURE:
  <223> OTHER INFORMATION: Synthesised forward primer of BC3

<400> SEQUENCE: 5
cgccaagcgg gtacgcttca ccg                                          23

<210> SEQ ID NO 6
  <211> LENGTH: 22
  <212> TYPE: DNA
  <213> ORGANISM: Artificial Sequence
  <220> FEATURE:
  <223> OTHER INFORMATION: Synthesised reverse primer of BC3

<400> SEQUENCE: 6
```

```
agaaatataa gttttaaaga ag                                            22
```

<210> SEQ ID NO 7
<211> LENGTH: 990
<212> TYPE: DNA
<213> ORGANISM: Bacillus coagulans

<400> SEQUENCE: 7

```
cagggctttc agatacccgt atgatccttg ggtattgtgc tgccttttca aattttggct    60
tgcggaaccc cgctgtttcc gcaaccggca ccggtttttt caacggggga tcggaatgcg   120
actcagatac ccgtatgatc cttgggtatt gtgctgcctt tcaaatttt ggcttgcgga    180
accccgctgt ttccgcaacc ggcaccgttt tttcaaccgg ggaccagaa cgggacgcag    240
atatccatat gttccgtata tggaagcgga ttgttttaca gcttcgggaa cagcccgtgg   300
atgccgcttg cgatcatttg aaccgccatg acggcaagaa tcagccccat cagccttgtt   360
ataatgttaa ggccgctttg cccgagctta gagataatcg aagatgaata ataaaacaat   420
acaaaggtta aagcgagcac aatggtatag ccgattaaaa cacttgccag gtttggcagg   480
gaatgggaag acgtctgcgc catgacggtt gcgatcgtcc cgggcccggc caggatcggg   540
agggcaagcg gtgtaataga gatgtcatcc cgggcttcaa cttctttccg ctcattcgga   600
tgcgggcttt gcgatcttgc attttttagcg tgcagcaggc tgtaggcaat cccgaagatt   660
aagatccccc ctgcaacgcg aaacgcatga atcgtaatcc cgaagacctc gaacaataat   720
tttccaagaa aaagaaaaac cgttagtatg ataaagaaa caatgaccgc tttgcgggcg    780
gttttccgtt tgtccttaa ggaatatcca ccagttaatg aaatgaagat tggaatattc    840
ccgatcggat tcatcaccgc aaaaaaaccg agcgaaagtt ttataatttc gccgaacaat   900
ttctacaccc cttttttgttt attttttatt gcattaccct gttggtggaa aatgtaacag   960
gggtaacagt tttttgatgg acggatcccc                                    990
```

<210> SEQ ID NO 8
<211> LENGTH: 543
<212> TYPE: DNA
<213> ORGANISM: Bacillus coagulans

<400> SEQUENCE: 8

```
gaatgcatta tgcaacatgg gcaattggac attcatccaa acacgattgc gctgattcct    60
tgtcaggagg ggggagaaaa agggaccaaa atattggaag tggatcggga acgatttgtg   120
ccggaacttc ccctgaatat cgtgaaaaaa agctgcaaat actttggaag cgattacgaa   180
ggaagaaaaa atgcgacaaa aagcctgatt catgtccggc acaagccgcc gatcctcgtc   240
gatccccata cagctaccat acttttttcca acaaaatcgc ccagccagcc ggattgtatt   300
tggctgatct ccggacatat taaagaccac accccagaag gcaaaaaaac tgaagtggtt   360
ttttcaaaca atcaatcact cgtgttgcca atcagctatg gatcgtttat caatcagtac   420
cataaagcgg ctgctttgca ggttgcttat gaaatcaaca tccgacgctc ccggatgcaa   480
ttcttgaaac aacagggata cagggcgatg gaagagagcg ggctgtattg gatttaagcc   540
tgg                                                                 543
```

<210> SEQ ID NO 9
<211> LENGTH: 3010
<212> TYPE: DNA
<213> ORGANISM: Bacillus coagulans

<400> SEQUENCE: 9

```
cgccaagcgg gtacgcttca ccgggctgag cccgcgtacc ttacagcgat gggagacagt    60
ccactaaaaa agtcttgttt tgctatttac gttccaaatt tcagctgcat acctgagcac   120
ggtataatcc gatgaaaata caccggcatt ggcgatattg atcaatgcca tctcctgcca   180
tttgagcgga tcgcgtaca gcatgtccac ttttttctgc gccagcgcgt aatcctcgaa    240
atctcttaaa acaaaaaact catcaccata tttaatgagg gaatcaaaga tgtcccgccc   300
ttccgcctgc acaccgggaa tcgagccgtc aatcagcgca tcgagtacac ggtgcagcac   360
cggatttttc ttataataat cataggaatg ataagaccgg tcatggtaat attggaaaac   420
ttcctgatcg gtcagcccga agagaataat attgtcttcc cccacgaggt cgcggatttc   480
cacatttgca ccgtccagcg tggccaatgt aaccgcgcca ttgagcataa atttcatatt   540
gctcgttccg gaggcttcct tggatgcgag tgaaatctgt tcgctgacgt ctgccgccgg   600
gatgatccgc tcggccagcg acacaccgta attttcgata aaaacgatct tcagcatatc   660
cctgactgcc gggtcatggt taatgagatc cgctgcggcg tttatcaact taatgatttc   720
cttggcgtaa gtgtagctcg gtgccgcttt gccgccaaag atgaaaacgc gcgggtaaat   780
atctgctccc ggatcatcct tcaatttaaa atacaagctt aaaatatgca aaagattcaa   840
aagctgcctt ttataagcat ggaaacgttt gacctgcaca tcaaaaatgg catctgtcca   900
gacggcgagc cctgtccttt tcctaatata gtctgccagc cgttgcttat tgatttgttt   960
gatttccgca agttgccgca ggacgttttc atcccggcga aaaggctcca gcattttcag  1020
gtctgtcggc tttgtcgccc actccttgcc gattttgctg tcaataaaac tgcgcagcgg  1080
ttcgttggaa agcagcagcc agcgccggtg agtaatgccg tttgttttat tattaaatct  1140
ggacgggaaa atgtgataga agtcacgaag cacttttttct ttcaaaatat tcgtatggag  1200 cttttgccacc ccgttgatgc tatggctgcc aatgattgcc aggtgcgcca tcttcacgct  1260
cccgcccgaa attaccctcg tccgctcaat catatcccag tcatataaac gggccatgtc  1320
ctcggcatag cggcggtcaa tctcgcaaat aatttgataa atgcgcggca aaagctgtgc  1380
catcatatct gtcggccaac tttcgagcgc ttcggacata atggtatggt tggtatagct  1440
gagcactttt accgtaacat cccaggccgg ttcccagtcc atgccttcct cgtccatcaa  1500
aatacgcatt agttcaggga cacataatgc cgggtgtgta tcattgatgt ggatggcgac  1560
tttttcggcg agattggaca tcggcaggcc gcgtttttta taggtgcgga taatgctttg  1620
aatgcctgct gagacgaaaa aatattcctg tttcaaacgt aacagacgcc cttcataatt  1680
ggaatcgtca ggatacagca cttccgaaat gctttcgatc cggctttgct gctgaataaa  1740
agcatggtac tccgtgttcg catcctcaag cggcatttcc gccgaccata atcttaaagt  1800
gttgaccgta ttgtccccgt aaccgattac cggggtatca tacggcacgg caagtacaat  1860
ttcctcattt tcataatggg gaacaaaatg ccccgatgca tctttctcaa gccggacgtt  1920
gccgtaaaac cgcacatttta ccgccttgtt cagccggcgt gtctcccaca cattgccgtt  1980
tcgcagccag ttttcaggca gttcaacctg gtagccgttg acaaattttt gcctgaaaag  2040
cccgtactta aaacggatgc cgttcccgtg cccggggatc gcatgtgtcg ccattgaatc  2100
gatgaaacaa gctgccagcc ggccaagacc gccgttcccc agtccggcat ccagttccac  2160
ctgttccaac gcttccaggt ccatccccat ttctttaagc cccgcccgga ccgtatcgag  2220
aattccgagg ttgaacaaat tactttttcaa catcctgcca agcaaaaatt ccattgaaaa  2280 atagtaaaact tgttttttccc cttttttccaa gtagcgctga ttcgtgttcc gccattcttt  2340
```

```
tgctgcataa gaaccgatca attttccgag tgtaacatac tgctctgtca aatcagattt    2400
ttccacatcc attgtgaagt agtccgacag cattctttcg aaatcggcct taaattgttc    2460
ctttgtgagt tccatcccat ttcctcccgt tttttgcccg taatgtaacc ctttctccgg    2520
agaggctcag agccgttcct gactattttt tcaaatgctg attcttcatt ttcctgattt    2580
ttatgatttt ataaatagca aatccggcgg cacagagaaa aatgagccag cccaactgaa    2640
ataccacatc aggccaattg acatatgtat gcatgctttt ctctcctcca taagggaatt    2700
tcctttttca aaaatttgt tcatcatctt cctagtttta ttttaatgga cgccggagcc     2760
attgtcaccg aaaacttttt gccggcgtcc taaagcccct ttgcaaagtg gccgctgctc    2820
catcggtttc tcgcgtgcca accgtcacgg tgtgtcgtgg ggaggagcaa aattcactcc    2880
caaaaatttt tggatctcta ttcccatttt tggctaaacc tataaaaggc gccaaccaaa    2940
aaagcaccca aagccgggat ttctgctttg ggcgcttctt ctttaaaact tatatttctt    3000
cacaatctcc                                                          3010
```